(12) United States Patent
Van Antwerp et al.

(10) Patent No.: US 7,323,543 B2
(45) Date of Patent: Jan. 29, 2008

(54) MULTIPLE AGENT DIABETES THERAPY

(75) Inventors: William P. Van Antwerp, Valencia, CA (US); Andreas H. R. Pfuetzner, Maint (DE)

(73) Assignee: MiniMed, Inc., Sylmar, CA (US)

( * ) Notice: Subject to any disclaimer, the term of this patent is extended or adjusted under 35 U.S.C. 154(b) by 79 days.

(21) Appl. No.: 11/166,390

(22) Filed: Jun. 24, 2005

(65) Prior Publication Data

US 2006/0074013 A1 Apr. 6, 2006

Related U.S. Application Data

(62) Division of application No. 09/344,676, filed on Jun. 25, 1999, now abandoned.

(51) Int. Cl.
*C07K 14/605* (2006.01)
(52) U.S. Cl. .............................. 530/308; 514/2; 514/3; 514/12; 514/342; 530/303; 530/304
(58) Field of Classification Search ................... 514/3, 514/4, 342, 12; 530/303, 304, 308
See application file for complete search history.

(56) References Cited

U.S. PATENT DOCUMENTS

| | | | |
|---|---|---|---|
| 4,652,548 | A | 3/1987 | Chance et al. |
| 4,988,675 | A | 1/1991 | Froesch et al. |
| 5,149,777 | A | 9/1992 | Hansen et al. |
| 5,514,646 | A | 5/1996 | Chance et al. |
| 5,527,307 | A | 6/1996 | Srisathapat et al. |
| 5,569,186 | A | 10/1996 | Lord et al. |
| 5,637,095 | A | 6/1997 | Nason et al. |
| 5,641,744 | A | 6/1997 | Cooper |
| 5,753,681 | A | 5/1998 | Fujiwara et al. |
| 5,783,556 | A | 7/1998 | Clark et al. |
| 5,958,909 | A | 9/1999 | Habener |
| 6,136,784 | A | 10/2000 | L'Italien et al. |
| 6,153,632 | A | 11/2000 | Rieveley |
| 6,166,042 | A | 12/2000 | Ikeda et al. |
| 6,166,043 | A | 12/2000 | Ikeda et al. |
| 6,169,099 | B1 | 1/2001 | Ikeda et al. |
| 6,169,100 | B1 | 1/2001 | Ikeda et al. |
| 6,268,343 | B1 | 7/2001 | Knudsen et al. |
| 2003/0054979 | A1 | 3/2003 | Kim et al. |

FOREIGN PATENT DOCUMENTS

| WO | 9220366 | 11/1992 |
|---|---|---|
| WO | 9602270 | 2/1996 |
| WO | 9857636 | 12/1998 |
| WO | 9943705 | 9/1999 |

OTHER PUBLICATIONS

O. Molcuda et al., "Plasma Glucose Response After Intravenous Injection of Tolbutamide in Insulin- Treated Type I and Type II Diabetic Patients", *Exp. Clin. Endocrinol.*, vol. 91, No. 3, 1988, pp. 265-270.
J. Holst, "GLP-1 in NIDDM", *Diabetic Med.*, (9 Suppl. 6) Sep. 13, 1996, pp. S156-60.
A. Ryan et al., "Inslunotropic Hormone Glucagon-Like Peptide-1-(7-37) Appears not to Augment Insulin-Mediated Glucose Uptake in Young Men During Euglycemia", *J. of Clin. Endocrinology and Metabolism*, vol. 83, No. 7, pp. 2399-2404.
B. Ahren et al., "Effects of Glucagon-Like Peptide-1 on Islet Function and Insulin Sensitivity in Noninsulin-Dependent Diabetes Mellius", vol. 82, No. 2, pp. 473-478.
M. Toft-Nielsen et al., "The effect of Glucagon-Like Peptide I (GLP-I) on Glucose Elimination in Healthy Subjects Depends on the Pancreatic Glucoregulatory Hormones", *Diabetes*, vol. 45, May 1996, pp. 552-556.
M. Cumiak, M.D., et al., "Antidiaborogenic Effect of Glucagon-Like Peptide-1 (7-36) Amide in Normal Subjects and Patients with Diabetes Mellitus" *The New England Journal of Medicine*, May 14, 1992, pp. 1316-1322.
U. Grau, "Life Support Systems, 1986," Suppl. 1, Proc.—Eur. Soc. Artif. Organs, Annu. Mecr., 12th, 1985, 551-5.
H.M. Walter, Diabetes Research, 13(2):75-7, 1990.
Zhang, Science, 284:974-977, 1999.
Grau, Diabetes, 36(12):1453-1459, 1987.
J. Reif, Langmuis, 17(19):5801-5812, 2001.
H. Thurow, Diabetologia, 27(2):212-218, 1984.
G. Stangl, International Journal of Environmental Analytical Chemistry, 58(1-4):15-22, 1995.

*Primary Examiner*—David Lukton
(74) *Attorney, Agent, or Firm*—Gates & Cooper LLP

(57) ABSTRACT

A pharmaceutical composition includes at least two of agents I)-iii), wherein agent i) is selected from the group consisting of an insulin, an insulin analog, a physiologically active fragment of said insulin and a physiologically active fragment of said insulin analog, agent ii) is selected from the group consisting of an insulin-related peptide, an insulin-related peptide analog, a physiologically active insulin-related peptide fragment and a physiologically active insulin-related peptide analog fragment, and agent iii) is an insulin sensitizer.

7 Claims, No Drawings

MULTIPLE AGENT DIABETES THERAPY

This application is a divisional of U.S. patent application Ser. No. 09/344,676, filed Jun. 25, 1999 now abandoned, the entire contents of which is incorporated herein by reference.

FIELD OF THE INVENTION

The present invention relates to pharmaceutical compositions useful in the treatment of diabetes, and more particularly to compositions useful in treating both diabetes and one or more side effects thereof. The present invention also relates to methods of treating diabetes using such compositions.

BACKGROUND OF THE INVENTION

Diabetes mellitus is a metabolic disorder characterized by chronically elevated levels of blood glucose, or hyperglycemia, which results from a reduction or absence of activity of the peptide hormone insulin. Insulin, which is produced and secreted by the beta cells of the pancreas, promotes the utilization of glucose and is essential to the maintenance of blood levels of glucose within the normal physiological range.

Included within the scope of the term diabetes mellitus are two states: Type 1, also known as insulin-dependent diabetes mellitus (IDDM), and Type 2, or non-insulin-dependent diabetes mellitus (NIDDM). Type 1 diabetes is characterized by a deficiency or absence of insulin, such that the level of blood glucose cannot be maintained within the normal range, and must be treated by administration of insulin to the patient. Type 2 diabetes is characterized by either or both a state of insulin resistance or impaired insulin sensitivity or reduced insulin secretion, that is, a state in which insulin does not produce the expected decrease in blood glucose concentrations, resulting in hyperglycemia.

Insulin and insulin analogs are commonly administered to diabetic patients, particularly Type 1 patients, in an injectable composition which comprises a pharmaceutically acceptable carrier and typically one or more conventional excipients. It is believed to be desirable to include in such compositions one or more peptides, in particular peptides that are naturally secreted by the pancreas together with insulin in non-diabetics. Such peptides are herein referred to as "insulin-related peptides".

One problem that is expected to arise in preparing such compositions is that most peptides are not as stable thermally as insulin. A need therefore exists for a thermally stable composition that includes insulin or an insulin analog together with at least one insulin-related peptide, peptide fragment or peptide analog.

Certain therapies for Type 2 diabetes do not require the administration of insulin. Such therapies, however, typically act by stimulating the release of insulin from the pancreatic beta cells. In these therapies, the pancreas can be subjected to undesirable stress. A need therefore also exists for an improved composition that does not cause excessive stress to the pancreas of the patient to whom the composition is administered.

A need also exists for method of preparing such compositions and administering such compositions to a patient.

SUMMARY OF THE PREFERRED EMBODIMENTS

In accordance with one aspect of the present invention, there is provided a pharmaceutical composition that includes at least two of agents chosen from the group of agents i)-iii). In the inventive composition, agent i) is selected from the group consisting of an insulin, an insulin analog or a physiologically active fragment of the insulin or insulin analog, agent ii) is selected from the group consisting of an insulin-related peptide, an insulin-related peptide analog, a physiologically active insulin-related peptide fragment, or a physiologically active insulin-related peptide analog fragment, and agent iii) is an insulin sensitizer.

According to one more particular embodiment, the inventive composition includes agents i) and ii) above. More particularly, the composition further includes a pharmaceutically acceptable non-ionic surfactant.

According to another more particular embodiment, the inventive composition includes agents i) and iii) above.

According to another more particular embodiment, the inventive composition includes agents ii) and iii) above. This embodiment is beneficially employed in treating Type 2 diabetes.

In accordance with another aspect of the present invention, there is provided a pharmaceutical composition that includes at least one agent selected from the group consisting of an insulin, an insulin analog, a physiologically active insulin fragment and a physiologically active insulin analog fragment, and at least one agent selected from the group consisting of an insulin-related peptide, an insulin-related peptide analog, a physiologically active insulin-related peptide fragment and a physiologically active insulated-related peptide analog fragment. The second agent has a hydrophobic portion that is coated with a pharmaceutically acceptable non-ionic surfactant.

In accordance with a further aspect of the present invention, methods of treating diabetes are provided that include the step of administering to a patient in need of such treatment the foregoing pharmaceutical compositions.

According to more specific embodiments, the compositions are administered to the patient by a medication infusion pump. Preferably, the compositions are continually administered to the patient.

In accordance with still another aspect of the present invention, a method of treating diabetes is provided that includes the step of administering to a patient in need of such treatment at least two pharmaceutical compositions chosen from the group of compositions a)-c). Composition a) includes at least one insulin, insulin analog or fragment thereof as described herein. Composition b) includes at least one insulin-related peptide, peptide analog or fragment thereof. Composition c) includes at least one insulin sensitizer. Each composition also includes a pharmaceutically acceptable carrier.

In more specific embodiments, each composition is administered using a separate delivery device, in particular an external or internal medication infusion pump, and at different rates. Preferably each composition is administered continually.

In one particular preferred embodiment, compositions a) and b) are administered to the patient. In this embodiment, composition b) preferably further includes at least one pharmaceutically acceptable non-ionic surfactant.

Methods of making the inventive compositions are also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

It has been discovered that the administration of two or more distinct types of agent, in multiple agent pharmaceutical compositions as described herein or in separate compositions that are coadministered or sequentially administered, e.g, via medication infusion pumps, is effective in treating both diabetes and one or more diabetes side-effects.

As used herein, an "insulin analog" is a peptide that has insulin-like physiological activity, i.e., binds an insulin receptor and lowers blood glucose, and that includes one or more amino acids different from the amino acid sequence of a naturally occurring insulin. Likewise, an "insulin-related peptide analog" is a peptide that has the physiological activity of an insulin-related peptide and an amino acid sequence that differs in at least one position from the amino acid sequence of the insulin-related peptide. A "physiologically active fragment" of an insulin, insulin analog, insulin-related peptide or insulin-related peptide analog is a molecule that includes less than the full amino acid sequence of the respective peptide but that has substantially the same physiological activity as the complete peptide, preferably at least about 70% of the activity of the complete peptide.

Also as used herein, an "insulin sensitizer" is a compound that increases a patient's response to, or decreases the patient's resistance to, insulin.

For present purposes, all references to "insulin", "insulin analog" and "insulin-related peptide" will encompass analogs and physiologically active fragments of such molecules.

A first preferred embodiment of the inventive pharmaceutical composition combines therapeutically effective amounts of an insulin with an insulin-related peptide. More preferably, this embodiment also includes a non-ionic surfactant. Use of non-ionic surfactants according to the invention affords thermally stable compositions. Non-ionic surfactants according to the invention are used to create safe domains which protect the relatively more thermally unstable insulin-related peptides. The protection afforded by the surfactants enables effective co-administration of the insulin and the selected insulin-related peptide.

The inventive compositions according to this embodiment preferably include an insulin selected from the group consisting of human insulin, porcine insulin and bovine insulin. Combinations of two or more different insulins can also be used. The insulin can be a naturally occurring insulin, a semisynthetic insulin, a synthetic insulin or a recombinant insulin.

Insulin analogs that are useful according to the invention include, without limitation, "Lyspro" (commercially available from Eli Lilly Co.), Lys$^{B28}$ insulin, Pro$^{B29}$ insulin and Asp$^{B28}$ insulin. Other insulin analogs that are useful according to the invention are described, e.g., in U.S. Pat. Nos. 5,149,777 and 5,514,646, which are incorporated herein by reference. Combinations of two or more insulin analogs can also be used.

Insulin-related peptides that are useful according to the invention include, without limitation: C-peptide, which is useful in protecting microvasculature against glycosylation-related damage, and which in addition delays gastric emptying; GLP-1, which also delays gastric emptying; amylin; IGF-1, which functions to maintain glucostasis; and IGF-1 bound to binding protein 3 (somatokine), which does not produce hyperglycemia and is therefore particularly useful for treating type 2 diabetes.

Non-ionic surfactants useful according to this embodiment of the invention include, without limitation, block copolymers of propylene oxide and ethylene oxide. Exemplary surfactants include those commercially available from the BASF Corporation under the name Pluronic®, such as Pluronic F20, Pluronic F28, Pluronic F68, Tween 20, Tween 40 and Brij, and those commercially available under the name Genapol@, such as Genapol 1800. The non-ionic surfactant preferably is pharmaceutically acceptable. Combinations of two or more non-ionic surfactants can also be used.

When a non-ionic surfactant is used, preferably, the amount of the non-ionic surfactant in the composition is less than that which results in a two-phase composition. That is, the concentration of the surfactant in the composition is below the critical micellar concentration of the composition. The critical micellar concentration will vary depending on the particular agents used to form the composition, but is readily determined by those skilled in the art through routine experimentation.

Thus, in the foregoing preferred embodiment, the inventive composition preferably includes about 1.5 to about 40 mg/ml of the insulin or combination of insulins, more particularly about 3.5 to 3.5 mg/ml, about 1.5 to about 40 mg/ml, more particularly about 4 to 10 mg/ml, of the selected insulin-related peptide(s), and an amount of the selected surfactant(s) such that the concentration of the selected surfactant in the composition is less than the critical micellar concentration.

At lower surfactant concentrations, a "micro" two-phase composition is formed in which the surfactant coats the hydrophobic portions of the insulin-related peptide. This surfactant coating also increases the thermal stability of the peptide. Thus, in another preferred embodiment of the invention, a pharmaceutical composition is provided which includes i) an insulin and ii) an insulin-related peptide that includes a hydrophobic portion that is coated with a non-ionic surfactant. The amount of the non-ionic surfactant present in the composition preferably is sufficient to completely coat all hydrophobic portions of the insulin-related peptide.

A more specific preferred embodiment of the foregoing pharmaceutical composition further includes a therapeutically effective amount of at least one insulin sensitizer. Preferred insulin sensitizers include compounds of the glitazone family. These include, for example, the compounds described in U.S. Pat. No. 5,753,681, incorporated herein by reference, such as troglitazone, pioglitazone, englitazone and related compounds. When insulin sensitizers are included in the foregoing pharmaceutical composition, they preferably are present in amounts ranging from 0.2 to 1.4 mg/ml, more preferably about 0.5 to 0.8 mg/ml.

According to a second preferred embodiment, the inventive pharmaceutical composition includes an insulin and an insulin sensitizer (i.e., agents i) and iii)). The amounts of the insulin and insulin sensitizer are typically the same as those set forth in connection with the preceding embodiment, i.e., about 1.5 to 40 mg/ml, more particularly about 3.5 to 14 mg/ml of an insulin or combination of insulins, and about 0.2 to 1.4 mg/ml, more particularly about 0.5 to 0.8 mg/ml of one or more insulin sensitizers.

According to a third preferred embodiment, the inventive pharmaceutical composition includes an insulin-related peptide and an insulin sensitizer (i.e., agents ii) and iii)). The amounts of the insulin and insulin sensitizer are typically the same as those set forth in connection with the preceding embodiment, i.e., about 1.5 to 40 mg/ml, more particularly about 4 to 10 mg/ml of an insulin-related peptide or combination of insulin-related peptides, and about 0.2 to 1.4 mg/ml, more particularly about 0.5 to 0.8 mg/ml of one or more insulin sensitizers.

The inventive compositions are preferably formulated to include one or more pharmaceutically acceptable carriers and optionally additional conventional excipients such as diluents, buffers, preservatives, pH adjusters, etc. The compositions can be prepared by a variety of known techniques, for example those described in *Remington's Pharmaceutical Sciences,* 17th Edition, Mack Publishing Company, Easton, Pa., USA (1985), which is incorporated herein by reference.

The inventive compositions are particularly useful in treating patients suffering from diabetes together with one or more diabetes side effects. The compositions can be administered to patients in need of such treatment by any desired route, such as subcutaneous, pulmonary, etc. In particular, the inventive compositions can be administered by means of medication infusion pumps, which can be reusable or non-reusable (i.e., disposable), and implantable or externally mountable. Medication infusion pumps that are usefully employed for this purpose include, without limitation, the pumps disclosed in copending, commonly assigned U.S. patent applications Ser. Nos. 09/253,382 and 09/253,383, filed Feb. 19, 1999; in U.S. Pat. No. 5,637,095, to Nason et al., entitled "Medication Infusion Pump with Flexible Drive Plunger"; in U.S. Pat. No. 5,569,186, to Lord et al., entitled "Closed Loop Infusion Pump System with Removable Glucose Sensor"; and in U.S. Pat. No. 5,527,307, to Srisathapat et al., entitled "Implantable Medication Pump with Implantable Pressure Reservoir". The compositions can be administered continually from such devices, or can be administered intermittently.

According to one method of the invention, a pharmaceutical composition that includes two or more of agents i)-iii) as described is administered to a patient in need of such treatment.

According to an alternative method of treatment, two (or more) separate compositions are administered to the patient, either simultaneously or sequentially, and more specifically using separate delivery devices and delivery rates for each composition. Each such composition includes one (or more) of agents i)-iii) as described herein.

The invention is further illustrated by the following non-limiting examples.

EXAMPLE 1

| | |
|---|---|
| Insulin | 4 mg/ml |
| C-Peptide | 2.5 mg/ml |
| Genapol 1800 | 17 ug/ml |
| Glycerin | 16 mg/ml |
| Zinc | 0.36 mg/ml |
| Phosphate buffer | 1.96 mg/ml |

PH 7.4

The composition is suitable for administration using an externally mounted medication infusion pump.

EXAMPLE 2

| | |
|---|---|
| Insulin | 15.8 mg/ml |
| GLP-1 | 4.1 mg/ml |
| Pluronic F20 | 0.11 mg/ml |
| Glycerin | 16 mg/ml |
| Zinc | 0.36 mg/ml |
| Phosphate buffer | 1.96 mg/ml |

PH 7.0-7.8

The composition is suitable for administration using an implantable medication infusion pump.

EXAMPLE 3

| | |
|---|---|
| Insulin | 4 mg/ml |
| IGF-1 | 1.1 mg/ml |
| Tween 20 | 0.1 mg/ml |
| Glycerin | 16 mg/ml |
| Zinc | 0.36 mg/ml |
| Phosphate buffer | 1.96 mg/ml |

EXAMPLE 4

| | |
|---|---|
| Insulin | 4 mg/ml |
| IGF-1 bound to binding protein 3 | 2.2 mg/ml |
| Tween 40 | 0.1 mg/ml |
| Glycerin | 16 mg/ml |
| Zinc | 0.36 mg/ml |
| Phosphate buffer | 1.96 mg/ml |

EXAMPLE 5

| | |
|---|---|
| Lys$^{B28}$ Pro$^{B29}$insulin | 4 mg/ml |
| C-peptide | 2.5 mg/ml |
| Genapol | 0.01 mg/ml |
| Glycerin | 16 mg/ml |
| Zinc | 0.36 mg/ml |
| Phosphate buffer | 1.96 mg/ml |

EXAMPLE 6

| | |
|---|---|
| Insulin | 4 mg/ml |
| Troglitazone | 1.1 mg/ml |
| Phosphate buffer | 1.96 mg/ml |

EXAMPLE 7

| | |
|---|---|
| Insulin | 15.8 mg/ml |
| C-peptide | 2.5 mg/ml |
| Troglitazone | 1.0 mg/ml |
| Genapol | 0.01 mg/ml |
| Glycerin | 16 mg/ml |
| Zinc | 0.36 mg/ml |
| Phosphate buffer | 1.96 mg/ml |

In alternative embodiment, the insulin and/or insulin analog are replaced by an insulin mimetic material that functions to activate the human insulin receptor. Examples of suitable insulin mimetic materials are shown and described in U.S. Provisional Patent Application Ser. No. 60/135,278 filed on May 21, 1999 and entitled "Device and Method for Infusion of Small Molecule Insulin Mimetic Materials, which is specifically incorporated by reference herein and forms a part of this disclosure.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of treating diabetes comprising the step of administering to a patient in need of such treatment at least two pharmaceutical compositions (a)-(c), wherein:
   composition (a) comprises:
   (i) at least one agent selected from the group consisting of an insulin, an insulin analog, a physiologically active fragment of said insulin and a physiologically active fragment of said insulin analog, and
   (ii) a pharmaceutically acceptable carrier,
   composition (b) comprises:
   (i) at least one agent selected from the group consisting of an insulin-related peptide, an insulin-related peptide analog, a physiologically active insulin-related peptide fragment and a physiologically active insulin-related peptide analog fragment, and
   (ii) a pharmaceutically acceptable carrier, and
   composition (c) comprises:
   (i) an insulin sensitizer, and
   (ii) a pharmaceutically acceptable carrier,
   and wherein compositions (b) and (c) are required and administered concomitantly and further wherein the compositions administered in the method comprise GLP-1, troglitazone and Genapol 1800.

2. The method of claim 1 wherein each of said compositions is administered to said patient using a separate delivery device.

3. The method of claim 2 wherein each said delivery device is a medication infusion pump.

4. The method of claim 1 wherein each of said compositions is administered at a different rate.

5. The method of claim 1 wherein each of said compositions is administered continually.

6. The method of claim 1 wherein compositions (b) and (c) are administered to said patient.

7. The method of claim 1 wherein compositions (a), (b) and (c) are administered to said patient.

* * * * *